United States Patent
Venter et al.

(10) Patent No.: US 10,041,060 B2
(45) Date of Patent: *Aug. 7, 2018

(54) METHOD OF NUCLEIC ACID CASSETTE ASSEMBLY

(75) Inventors: J. Craig Venter, La Jolla, CA (US); Hamilton O. Smith, San Diego, CA (US); Clyde A. Hutchison, III, La Jolla, CA (US); Daniel G. Gibson, Crofton, MD (US)

(73) Assignee: Synthetic Genomics, Inc., La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/635,355

(22) Filed: Dec. 6, 2006

(65) Prior Publication Data

US 2007/0264688 A1    Nov. 15, 2007

Related U.S. Application Data

(60) Provisional application No. 60/742,542, filed on Dec. 6, 2005.

(51) Int. Cl.
| | |
|---|---|
| *C12Q 1/68* | (2018.01) |
| *C12N 15/10* | (2006.01) |
| *C12N 15/66* | (2006.01) |
| *C07H 21/02* | (2006.01) |

(52) U.S. Cl.
CPC ......... *C12N 15/10* (2013.01); *C12N 15/1093* (2013.01); *C12N 15/66* (2013.01)

(58) Field of Classification Search
CPC ..... C12N 15/10; C12N 15/1093; C12N 15/66
See application file for complete search history.

(56) References Cited

U.S. PATENT DOCUMENTS

| | | | |
|---|---|---|---|
| 5,750,380 A | 5/1998 | Itakura et al. | |
| 5,928,905 A | 7/1999 | Stemmer et al. | |
| 5,976,846 A | 11/1999 | Passmore et al. | |
| 6,492,114 B2 | 12/2002 | Arahira et al. | |
| 6,521,427 B1* | 2/2003 | Evans | 435/91.1 |
| 6,670,127 B2* | 12/2003 | Evans | 435/6 |
| 7,267,984 B2 | 9/2007 | Bennett | |
| 7,723,077 B2 | 5/2010 | Young et al. | |
| 7,803,539 B2 | 9/2010 | Yoo et al. | |
| 9,597,687 B2 | 3/2017 | Tegenfeldt et al. | |
| 2003/0087237 A1 | 5/2003 | Hong et al. | |
| 2003/0087238 A1* | 5/2003 | Evans | 435/6 |
| 2004/0096891 A1* | 5/2004 | Bennett | 435/6 |
| 2004/0185449 A1 | 9/2004 | Quinn et al. | |
| 2004/0235035 A1* | 11/2004 | Lathrop et al. | 435/6 |
| 2007/0037196 A1* | 2/2007 | Gibson et al. | 435/6 |
| 2014/0308710 A1 | 10/2014 | Qi et al. | |

FOREIGN PATENT DOCUMENTS

| | | | |
|---|---|---|---|
| WO | WO 98/38297 | * | 9/1998 |
| WO | WO 2007/032837 | | 3/2007 |
| WO | WO 2009/006598 A1 | | 1/2009 |
| WO | WO 2009/103027 A2 | | 8/2009 |
| WO | WO 2014/028895 A1 | | 2/2014 |

OTHER PUBLICATIONS

Smith et al., Proc. Natl. Acad. Sci. 100:15440-15445, 2003.*
Hutchison et al., Science 286:2165-2169, 1999.*
Gibson, D. G. et al., Science, vol. 319, pp. 1215-1220 (2008).*
Itaya, M. et al., PNAS USA, vol. 102, pp. 15971-15976, (2005).*
Holt, R. A. et al., Bioessays, vol. 29, pp. 580-590 (2007).*
Gerdes, S. et al., Curr. Opinion Biotechnol., vol. 17, pp. 448-456 (2006).*
Yus, E. et al., Science, vol. 326, pp. 1263-1268 (Nov. 2009).*
Guell, M. et al., Science, vol. 326, pp. 1268-1271 (Nov. 2009).*
Foley, P.L. et al., Biotechnol. Bioeng., vol. 105, pp. 26-36 (2010).*
Murtas, Mol. Biosystems, vol. 5, pp. 1292-1297 (2009).*
Strouboulis et al., Nucl. Acids Res., vol. 20, pp. 6109-6110 (1992).*
Schindelhauer, D. et al., Nucl. Acids Res., vol. 25, pp. 2241-2243 (1997).*
Tsuge, K. et al., Nucl. Acids Res., vol. 31, e133, pp. 1-8 (2003).*
New England Biolabs, "Properties of Exonucleases and Endonucleases", downloaded from www.neb.com/tools-and-resources/selection-charts/propeties-of-exonucleases-and-endonucleases?device=pdf on Aug. 12, 2014.*
New England Biolabs, "DNA Polymerase Selection Chart", downloaded from www.neb.com/tools-and-resources/selection-charts/dna-polymerase-selection-chart?device=pdf on Aug. 12, 2014.*
Kodumal, S. J. et al., PNAS USA, vol. 101, pp. 15573-15578 (2004).*
Herculase Hot Start DNA Polymerase Manual (downloaded from www.chemagilent.com/Library/usermanuals/Public/600310_A01.pdf on Aug. 12, 2014.*
Shevchuk, N. A. et al., Nucl. Acids Res., vol. 32, e19, pp. 1-12 (2004).*
Barnes, W.M., PNAS USA, vol. 91, pp. 2216-2220 (1994).*
Cheng, S. et al., PNAS USA, vol. 91, pp. 5695-5699 (1994).*

(Continued)

*Primary Examiner* — Teresa E Strzelecka
(74) *Attorney, Agent, or Firm* — DLA Piper LLP (US)

(57) ABSTRACT

Methods are provided for constructing a synthetic genome, comprising generating and assembling nucleic acid cassettes comprising portions of the genome, wherein at least one of the nucleic acid cassettes is constructed from nucleic acid components that have been chemically synthesized, or from copies of the chemically synthesized nucleic acid components. In one embodiment, the entire synthetic genome is constructed from nucleic acid components that have been chemically synthesized, or from copies of the chemically synthesized nucleic acid components. Rational methods may be used to design the synthetic genome (e.g., to establish a minimal genome and/or to optimize the function of genes within a genome, such as by mutating or rearranging the order of the genes). Synthetic genomes of the invention may be introduced into vesicles (e.g., bacterial cells from which part or all of the resident genome has been removed, or synthetic vesicles) to generate synthetic cells. Synthetic genomes or synthetic cells may be used for a variety of purposes, including the generation of synthetic fuels, such as hydrogen or ethanol.

21 Claims, 5 Drawing Sheets

(56) References Cited

OTHER PUBLICATIONS

Figure 1:
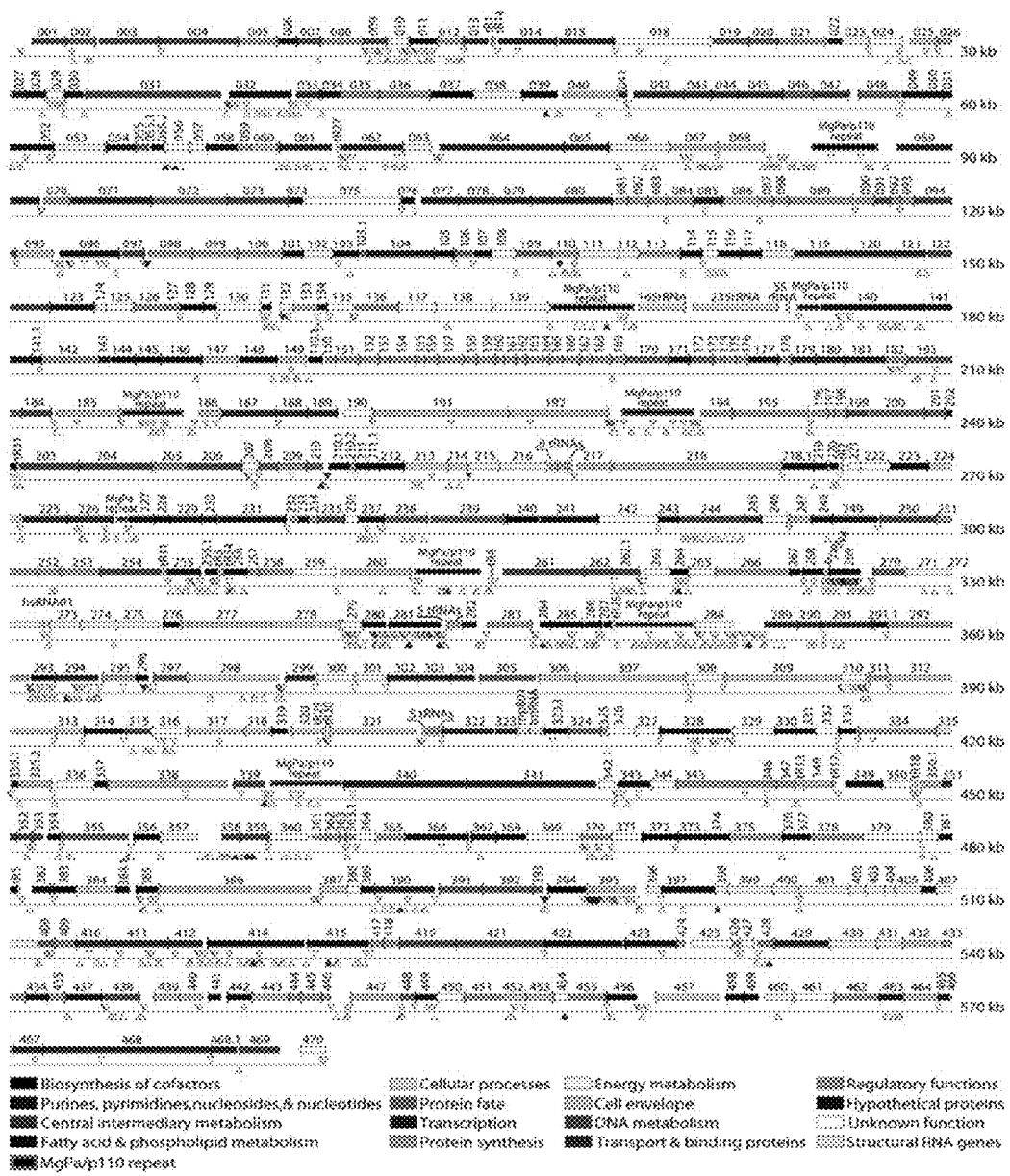
Figure 2:
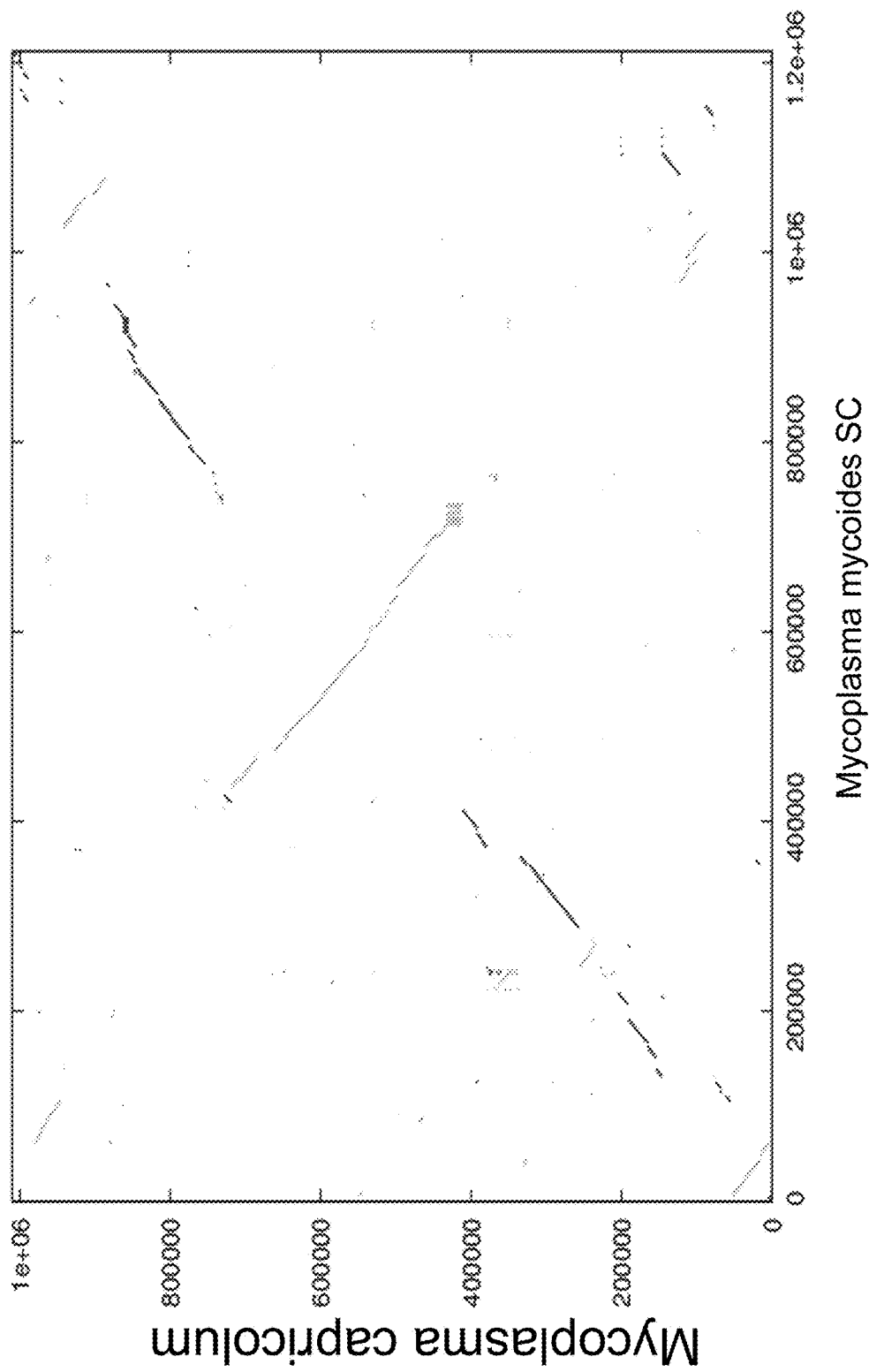

Glass et al., PNAS USA (2006) 103(2):425-430.
Marshall, Science (2002) 298(5599):1701.
Pennisi, Science (2003) 302(5649):1307.
Stemmer et al., Gene (1995) 164:49-53.
Supplementary European Search Report for EP 06851474.4, dated Mar. 10, 2009, 6 pages.
Tian et al., Nature (2004) 432(7020):1050-1054.
Young et al., Nucleic Acids Research (2004) 32:e59.
Check, Nature (2002) 420:350.
Griffiths et al. *An Introduction to Genetic Analysis*. 7th edition. New York: W. H. Freeman; 2000. Bacterial conjugation. Available from: "http://www.ncbi.nlm.nih.gov/books/NBK21942/".
Huang et al.: "*A 5'-3' Exonuclease from Saccharomyces cerevisiae Is Required for in Vitro Recombination between Linear DNA Molecules with Overlapping Homology*": Molecular and Cellular Biology, 13(6), Jun. 1993, pp. 3125-3134.
Barnes, W.M.: "*PCR Amplification of Up to 35-kb DNA with High Fidelity and High Yield from λ Bacteriophage Templates*;" Proc. Natl. Acad. Sci., 1994, 91: 2216-2220.
Brau, B., et al.: "*Cloning and Expression of the Structural Gene for Pyruvate Decarboxylase of Zymomonas mobilis in Escherichia coli*;"Arch. Microbiol., 1986, 144: 296-301.
Cheng, S., et al.: "*Effective Amplification of Long Targets from Cloned inserts and Human Genomic DNA*;" Proc. Natl. Acad. Sci., 1994, 91: 5695-5699.
Chomczynski, P., et al.: "*Alkaline polyethylene glycol-based method for direct PCR from bacteria, eukaryotic tissue samples, and whole blood*;"BioTechniques, 2006, 40: 454-458.
Gibson, D.G. et al.: "*Chemical Synthesis of the Mouse Mitochondrial Genome*;" Nature Methods, 2010, pp. 1-5.
Gibson, D.G., et al.: "*Enzymatic Assembly of DNA Molecules Up to Several Hundred Kilobases*;" Nature Methods, 2009, 6(5): 343-345, + Supplement.
Gibson, D.G., et al.: "*Complete Chemical Synthesis, Assembly, and Cloning of a Mycoplasma genitalium Genome*;"Science, 2008, 319(5867): 1215-1220.
Gibson, D.G..: "*Enzymatic Assembly of Overlapping DNA Fragments*;"Methods Enzymol., 2011, 498: 349-361.
Grunenwald, H.: "*Optimization of Polymerase Chain Reactions*;"Methods Mol. Biol., 2003, 226: 89-100.
Hughes, Randall A. et al.: "*Gene Synthesis: Methods and Applications*;"Enzymol. 2011; 498: 284-291.
Hutchison, C.A., et al.: "*Global Transposon Mutagenesis and a Minimal Mycoplasma Genome*;"Science, 1999, 286(5447): 2165-2169.

Kodumal, S.J., et al.: "*Total Synthesis of Long DNA Sequences: Synthesis of a Contiguous 32-kb Polyketide Synthase Gene Cluster*;" Proc. Natl. Acad. Sci., 2004, 101(44): 15573-15578.
Lareu, Ricky R. et al.: "*Emulating a Crowded Intracellular Environment In Vitro Dramatically Improves RT-PCR Performance*;" Biochem. Biophys. Res. Commun, 2007, 363: 171-177.
Lee, W.H.: "*Gene Synthesis from Oligonucleotides Mixtures by Solid Phase PCR and Assembly PCR in a Microfluidic Chip System*;"[dissertation]. Ann Arbor, MI: Univ of MI, 2010, pp. 1-8.
Lou, Xing Jian, et al.: "*Increased Amplification Efficiency of Microchip-Based PCR by Dynamic Surface Passivation*;"BioTechniques, 2004, 36: 248-252.
Richardson, S.M., et al.: "*GeneDesign: Rapid, Automated Design of Multikilobase Synthetic Genes*;"Genome, 2006, 16: 550-556.
Sasaki, Y., et al.: "*Effect of Molecular Crowding on DNA Polymerase Activity*;" Biotech. J., 2006, 1(4): 440-446.
Schindelhauer, D., et al.: *Efficient Combination of Large DNA In Vitro: In Gel Site Specific Recombination (IGSSR) of PAC Fragments Containing Alpha Satellite DNA and the Human HPRT Gene Locus*; Nucl. Acids Res., 1997, 25(11): 2241-2243.
Shevchuk, N. A., et al.: "*Construction of Long DNA Molecules using Long PCR-Based Fusion of Several Fragments Simultaneously*;" Nucl. Acids Res., 2004, 32(2): e19, 1-12.
Smith, H.O., et al.: "*Generating a Synthetic Genome by Whole Genome Assembly: φx174 Bacteriophage from Synthetic Oligonucleotides*;"Proc. Natl. Acad. Sci., 2003, 100(26): 15440-15445.
Strouboulis, J., et al.: "*Efficient Joining of Large DNA Fragments for Transgenesis*;" Nucl. Acids Res., 1992, 20: 6109-6110.
Tsuge, K., et al.: "*One Step Assembly of Multiple DNA Fragments with a Designed Order and Orientation in Bacillus subtilis Plasmid*;" Nucl. Acids Res., 2003, 31, e133: 1-8.
Withers-Martinez, C., et al.: "*PCR-Based Gene Synthesis as an Efficient Approach for Expression of the A+ T-Rich Malaria Genome*;" Prot. Eng., 1999, 12(12): 1113-1120.
Wu, Gang, et al.: "*Simplified Gene Synthesis: A One-Step Approach to PCR-Based Gene Construction*;"J. Biotechnol., 2006, 124: 496-503.
Ye, H., et al.: "*Experimental Analysis of Gene Assembly with TopDown One-Step Real-Time Gene Synthesis*;" Nucl. Acids Res., 2009, 37(7): e51.
Yus, E., et al.: "Impact of Genome Reduction on Bacterial Metabolism and its Regulation;" Science, 2009, 326(5957): 1263-1268.
Extended European Search Report dated Jul. 14, 2016, regarding EP 13863073.6.
International Search Report regarding PCT/US2013/074471.

* cited by examiner

Figure 3B:
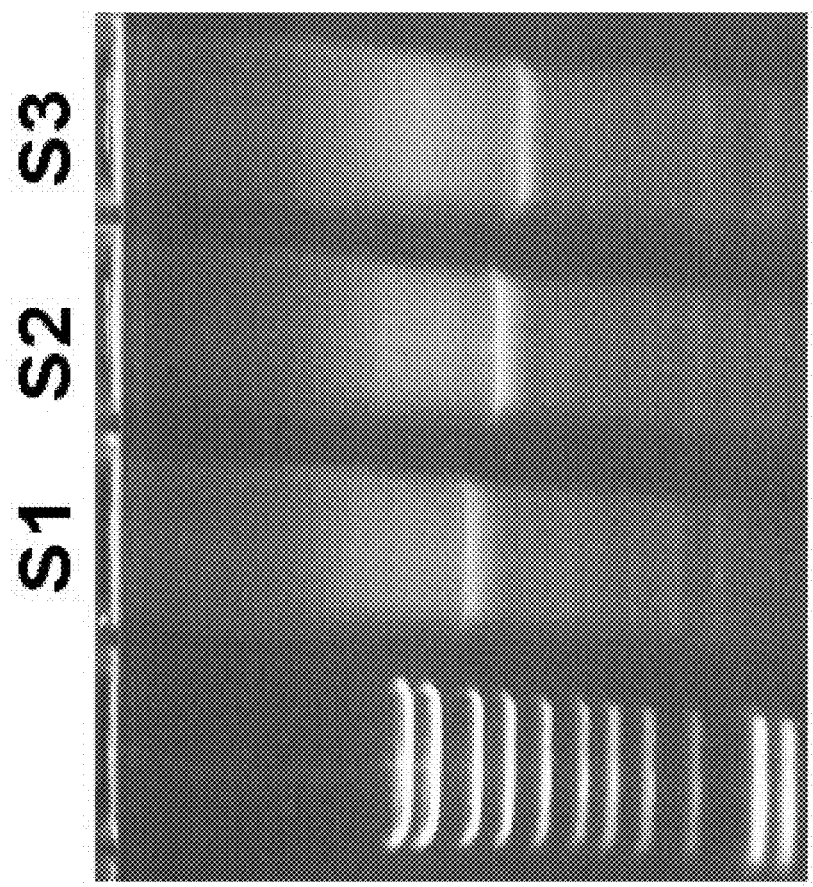
Figure 4:
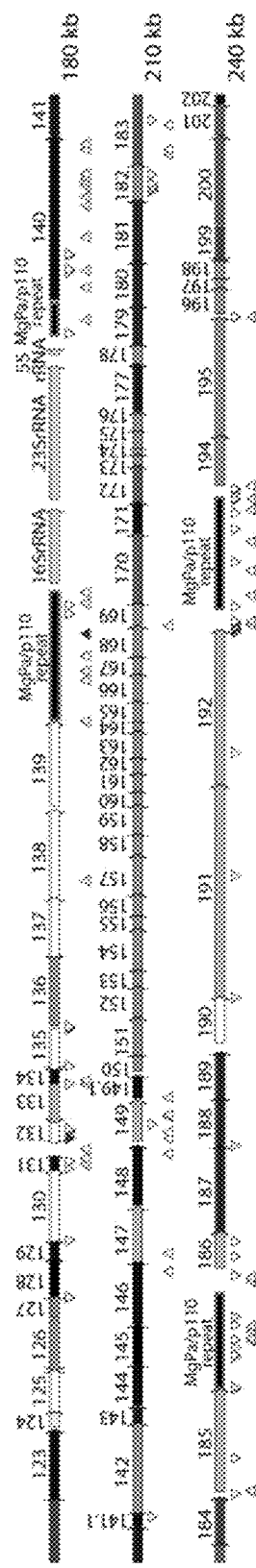

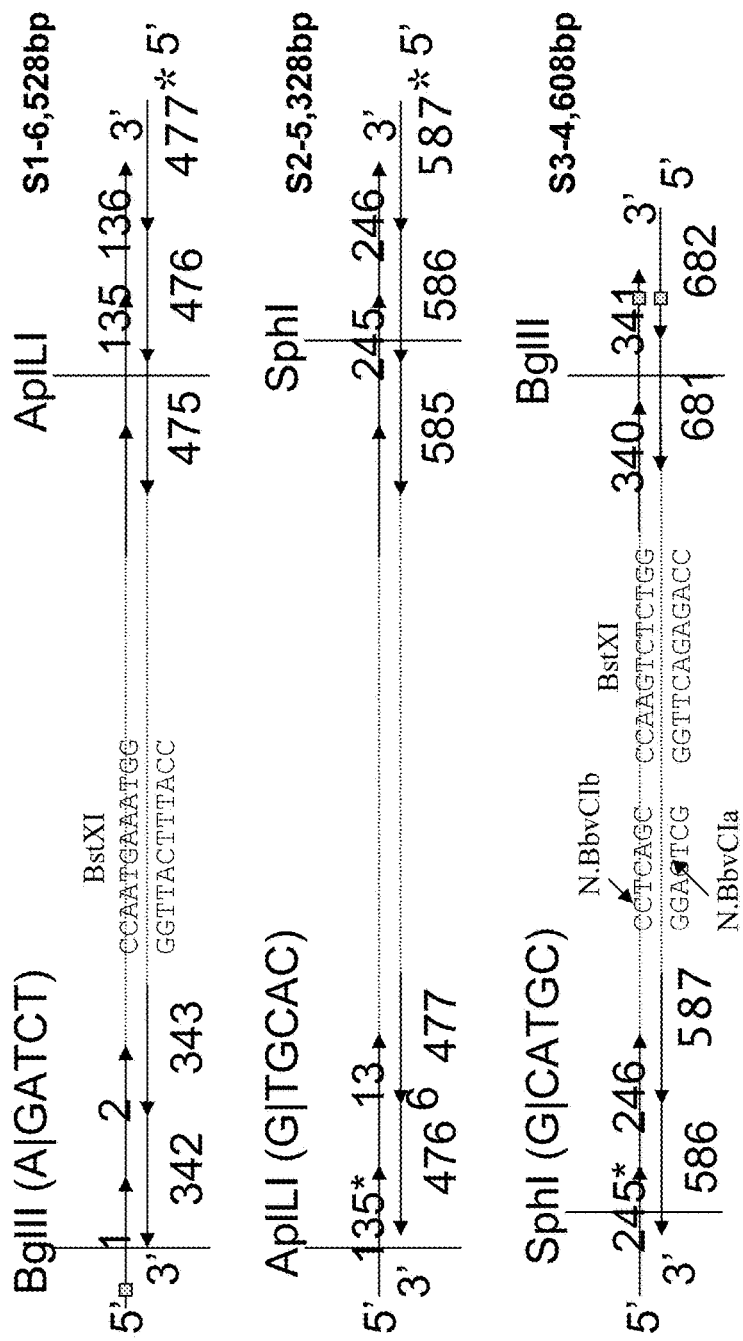
FIG. 3A: Scheme for mouse mitochondrial genome synthesis

SEQUENCE LISTING

```
<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
```

```
-continued

<223> OTHER INFORMATION: Synthetic construct

<400> SEQUENCE: 1
ccaatgaaat gg                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthetic construct

<400> SEQUENCE: 2
ccaagtctct gg                                                          12

<210> SEQ ID NO 3
<211> LENGTH: 12
<212> TYPE: DNA
<213> ORGANISM: Artificial Sequence
<220> FEATURE:
<223> OTHER INFORMATION: Synthetic construct

<400> SEQUENCE: 3
ccactgtgct gg                                                          12
```

METHOD OF NUCLEIC ACID CASSETTE ASSEMBLY

CROSS-REFERENCE TO RELATED APPLICATIONS

The present application claims benefit and priority from U.S. Provisional Patent Application Ser. No. 60/742,542 filed on Dec. 6, 2005, entitled, "Synthetic Genomes;" the present application is related to U.S. Provisional Patent Application Ser. No. 60/752,965 filed on Dec. 23, 2005, entitled, "Introduction of Genomes into Microorganisms;" U.S. Provisional Patent Application Ser. No. 60/741,469 filed on Dec. 2, 2005, entitled, "Error Correction Method;" and U.S. Non-Provisional patent application Ser. No. 11/502,746 filed on Aug. 11, 2006, entitled "In Vitro Recombination Method," all of which are incorporated herein by reference.

STATEMENT REGARDING FEDERALLY SPONSORED RESEARCH OR DEVELOPMENT

This invention was made with U.S. government support (DOE grant number DE-FG02-02ER63453). The government has certain rights in the invention.

REFERENCE TO SEQUENCE LISTING SUBMITTED VIA EFS-WEB

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows:

| File Name | Date of Creation | Size (bytes) |
|---|---|---|
| 616872001300Seqlist.txt | 8 Jun. 2009 | 4,096 bytes |

BACKGROUND OF THE INVENTION

Field of the Invention

The present invention relates generally to molecular biology, and more particularly to synthetic genomes.

Description of Related Art

Conventional genetic engineering techniques are limited to allowing manipulation of existing sequences. It would thus be desirable to have the ability to implement dramatic alterations and arrangements of genetic content, beyond that made possible by conventional techniques. Consequently, there is a need for synthetic genomes.

SUMMARY OF THE INVENTION

Embodiments and methods are provided for the design, synthesis, assembly and expression of synthetic genomes. Included are methods for rationally designing components of a genome; generating small nucleic acid fragments and assembling them into cassettes comprising portions of the genome; correcting errors in the sequences of the cassettes; cloning the cassettes (e.g., by in vitro methods such as rolling circle amplification); assembling the cassettes to form a synthetic genome (e.g., by methods of in vitro recombination); and transferring the synthetic genome into a biochemical system (e.g., by transplanting it into an intact cell, ghost cell devoid of functioning DNA, or other vesicle). In one embodiment, the synthetic genome comprises sufficient information to achieve replication of a vesicle (e.g., a cell) in which it resides. The technology extends to useful end products that a synthetic genomic system can produce, such as energy sources (e.g., hydrogen or ethanol), and biomolecules such as therapeutics and industrial polymers.

Included are methods for constructing a synthetic genome, comprising generating and assembling the nucleic acid components of the genome, wherein at least part of the genome is constructed from nucleic acid components that have been chemically synthesized, or from copies of chemically synthesized nucleic acid components. In one embodiment, an entire synthetic genome is constructed from nucleic acid components that have been chemically synthesized, or from copies of chemically synthesized nucleic acid components. Further, a synthetic genome may be a synthetic cellular genome (a genome which comprises all of the sequences required for replication of a vesicle (e.g., a cell or synthetic vesicle) in which it resides).

Methods are provided for constructing a synthetic cell, comprising use of certain exemplary methods to construct a synthetic genome and introducing (transplanting) the synthetic genome into a vesicle (e.g., a cell or a synthetic membrane bound vesicle). Another method includes constructing a self-replicating synthetic cell, comprising use of exemplary methods to construct a synthetic cellular genome and introducing (transplanting) the synthetic cellular genome into a vesicle (e.g., a cell or a synthetic membrane bound vesicle), under conditions effective for the synthetic cell to replicate. Further methods include producing a product of interest, comprising culturing an exemplary synthetic cell under conditions effective to produce the product. When the product is produced from a synthetic cell comprising a synthetic cellular genome, the genome is contacted with the vesicle under conditions effective to replicate the synthetic cell and to produce the product.

Other exemplary methods include making a synthetic cell, comprising removing part of or all of the resident (original) genome from a microorganism, such as a unicellular microorganism (e.g., a bacterium, fungus, etc.) and replacing it with a synthetic genome that is foreign to the organism (e.g., is from a different species of microorganism (e.g., bacterium)), which exhibits at least one property that is different from the resident genome. Various exemplary embodiments include a synthetic cell produced by this method.

One exemplary embodiment includes a synthetic genome that is capable of directing replication of a vesicle (e.g., cell) in which it resides, under particular environmental (e.g., nutritional or physical) conditions. In one embodiment, the cellular genome is supplemented in the vesicle (e.g., cell) by small molecules, such as nutrients, ATP, lipids, sugars, phosphates etc, which serve as precursors for structural features or substrates for metabolic functions; and/or is supplemented with complex components, such as ribosomes, functional cell membranes, etc. These additional elements may complement or facilitate the ability of the genome to achieve (e.g., program) replication of the vesicle/cell. In another embodiment, the sequences in the genome are capable of providing all of the machinery and components required to produce a cell and to allow the cell to replicate under particular energy or environmental (e.g., nutritional) conditions.

Further embodiments and methods include a "minimal genome" that may serve as a platform for introducing other sequences of interest, such as genes encoding biologic agents (e.g., therapeutic agents, drugs, vaccines or the like), or genes encoding products that, in the presence of suitable precursors, can produce useful compounds (e.g., biofuels, industrial organic chemicals, etc.). In one embodiment, the other sequences of interest result in the production of products in sufficient quantities to be commercially valuable.

According to one exemplary embodiment and method, a synthetic version of the *Mycoplasma genitalium* genome having 482 protein-coding genes and 43 RNA genes comprising a 580-kilobase circular chromosome is assembled from gene cassettes. Each cassette may be made from chemically synthesized oligonucleotides. Several versions of each cassette may be made such that combinatorial assembly into a complete chromosome results in millions of different genomes. These genomes may be tested for functionality by "genome transplantation," replacement of a cell's resident chromosome by the synthetic genome. According to further embodiments and methods, synthetic cells may be assembled from various subcellular components. Additionally, a genome in a cell-free environment may be established, comprising the necessary transcriptional and translation "machinery" to express genes.

BRIEF DESCRIPTION OF THE DRAWINGS AND EXAMPLES

FIG. 1 shows an illustration of suitable oligonucleotides for preparing *M. genitalium*. The triangles mark the position of transposon insertions (upper triangles are from Clyde A. Hutchison, III, et al. *Science* 286, 2165 (1999)). Vertical lines delineate the borders of the "5 kb" segments.

FIG. 2 illustrates the use of *mycoplasma* comparative genomics to identify genes that may be involved in a minimal gene set for *mycoplasma*. The figure displays a MUMMER comparison of the *M. capricolum* and *M. mycoides* genomes at the protein level showing the locations of orthologous genes. The cross pattern shows the conservation of gene position relative to the origin and terminus of replication for these two species.

FIG. 3A shows the design of 682 48-mer oligonucleotides, and the assembly of those oligonucleotides into three overlapping segments (cassettes), S1 (6,528 bp), S2 (5,328 bp), and S3 (4,508 bp), to assemble the mouse mitochondrial genome. The BstXI site in S1 (CCAATGAAATGG; SEQ ID NO: 1), BstXI site in S2 (CCAAGTCTCTGG; SEQ ID NO: 2), and a terminal BstXI site (CCACTGTGCTGG; SEQ ID NO: 3) are shown. FIG. 3B displays a gel containing products from an assembly of these pieces by the method described in Smith et al. (2003), modified to reduce the heating damage to the synthetic product. Taq ligations at 50° C. of the oligos for each mitochondrial fragment were subjected to 5 cycles of PCA and 20 cycles of PCR using end primers.

FIG. 4 shows the synthesis of 5 kb cassettes of an essential region of the *M. genitalium* genome.

DETAILED DESCRIPTION OF THE INVENTION

The following descriptions of various terms as used herein are not exhaustive and may include other descriptive matter.

"Cellular genome" or a "synthetic cellular genome" is a genome that comprises sequences which encode and may express nucleic acids and proteins required for some or all of the processes of transcription, translation, energy production, transport, production of cell membranes and components of the cell cytoplasm, DNA replication, cell division, and the like. A "cellular genome" differs from a viral genome or the genome of an organelle, at least in that a cellular genome contains the information for replication of a cell, whereas viral and organelle genomes contain the information to replicate themselves (sometimes with the contribution of cellular factors), but they lack the information to replicate the cell in which they reside.

"Foreign" gene or genome is a gene or genome derived from a source other than the resident (original) organism, e.g., from a different species of the organism.

"Genome" may include viral genomes, the genomes of organelles (e.g., mitochondria or chloroplasts), and genomes of self-replicating organisms, such as bacteria, yeast, archebacteria, or eukaryotes. A genome may also be an entirely new construct for an organism that does not fall into any known Linnean category. In one embodiment, the genes are from a microorganism, e.g., a unicellular microorganism, such as a bacterium. The genes may be in the order found in the microorganism, or they may be shuffled; and mutant versions of some of the genes may also be included.

"Membrane-bound vesicle," refers to a vesicle in which a lipid-based protective material encapsulates an aqueous solution.

"Minimal genome," with respect to a cell, as used herein, refers to a genome consisting of or consisting essentially of a minimal set of genetic sequences that are sufficient to allow for cell survival under specified environmental (e.g., nutritional) conditions. A "minimal genome," with respect to an organelle, as used herein, refers to a genome consisting of or consisting essentially of a minimal set of genetic sequences that are sufficient to allow the organelle to function. A minimal genome must contain sufficient information to allow the cell or organelle to carry out essential biological processes, such as, for example, transcription, translation, use of an energy source, transport of salts, nutrients and the like into and out of the organelle or cell, etc. A "minimal replicating genome," with respect to either a cell or an organelle, contains, in addition, genetic sequences sufficient to allow for self replication of the cell or organelle. Thus, a "minimal replicating synthetic genome" is a single polynucleotide or group of polynucleotides that is at least partially synthetic and that contains the minimal set of genetic sequences for a cell or organelle to survive and replicate under specific environmental conditions.

"Nucleic acid" and "Polynucleotide" are used interchangeably herein. They include both DNA and RNA. Other types of nucleic acids, such as PNA, LNA, modified DNA or RNA, etc. are also included, provided that they can participate in the synthetic operations described herein and exhibit the desired properties and functions. A skilled worker will recognize which forms of nucleic acid are applicable for any particular embodiment or method described herein.

"Synthetic genome," includes a single polynucleotide or group of polynucleotides that contain the information for a functioning organelle or organism to survive and, optionally, replicate itself where particular environmental (e.g., nutritional or physical) conditions are met. All or at least part of the genome (e.g., a cassette) is constructed from components that have been chemically synthesized, or from copies of chemically synthesized nucleic acid components. The copies may be produced by any of a variety of methods, including cloning and amplification by in vivo or in vitro methods. In one embodiment, an entire genome is constructed from nucleic acid that has been chemically synthesized, or from copies of chemically synthesized nucleic acid components. Such a genome is sometimes referred to herein as a "completely synthetic" genome. In other embodiments, one or more portions of the genome may be assembled from naturally occurring nucleic acid, nucleic acid that has been cloned, or the like. Such a genome is sometimes referred to herein as a "partially synthetic" genome.

Synthetic genomes offer numerous advantages over traditional recombinant DNA technology. For example, the selection and construction of synthetic genome sequences allow for easier manipulation of sequences than with classical recombination techniques, and permits the construction of novel organisms and biological systems. Furthermore, various embodiments and methods are amenable to automation and adaptation to high throughput methods, allowing for the production of synthetic genomes and synthetic cells by computer-mediated and robotic methods that do not require human intervention. The inventive technology opens the door to an integrated process of synthetic genome design, construction, introduction into a biological system, biological production of useful products, and recursive improvement to the design.

Various forms of rational or intelligent design of nucleic acids may be employed according to various exemplary embodiments and methods. According to one method, a gene set is identified that constitutes a minimal genome, e.g., of a bacterium, such as *Mycoplasma genitalia* (*M. genitalium*), *M. capricolumn* (e.g., subspecies *capricolum*), *E. coli*, *B. subtilis*, or others. One or more conventional or novel methods, or combinations thereof, may be used to accomplish this end. One method includes using random saturation global transposon mutagenesis to knock out the function of each gene in a microbial genome (e.g., a bacterial genome) individually, and to determine on this basis putative genes that may be eliminated without destroying cell viability. See, e.g., Smith et al. (1999) *Proc Natl Acad Sci USA* 87, 826-830. Another method is to use comparative genomics of a variety of related genomes (e.g., analyzing the sequences of orthologous organisms, metagenomics, etc.) to predict common genes which are basic to the function of a microorganism of interest (e.g., a bacterium). e.g., to identify genes common to all members of a taxon. Existing databases may be used, or new databases may be generated by sequencing additional organisms, using conventional methods. According to one method, the identification of genes in a minimal genome is facilitated by isolating and expanding clones of individual cells, using a method for disrupting cell aggregates. Example I herein illustrates the use of *mycoplasma* comparative genomics to identify genes that may be involved in a minimal gene set for *mycoplasma*.

Following the identification of a putative minimal set of genes required for viability and, optionally, replication under a defined set of conditions, a candidate minimal genome may be constructed as described herein. According to one method, a set of overlapping nucleic acid cassettes are constructed, each generally having about 5 kb, which comprise subsets of the genes; and the cassettes are then assembled to form the genome. The function/activity of the genome may be further studied by introducing the assembled genome into a suitable biological system and monitoring one or more functions/activities encoded by the genome. The synthetic genome may be further manipulated, for example, by modifying (e.g., deleting, altering individual nucleotides, etc.) portions of genes or deleting entire genes within one or more of the cassettes; by replacing genes or cassettes by other genes or cassettes, such as functionally related genes or groups of genes; by rearranging the order of the genes or cassettes (e.g., by combinatorial assembly); etc. The consequences of such manipulations may be examined by re-introducing the synthetic genes into a suitable biological system. Factors that may be considered include, e.g., growth rate, nutritional requirements and other metabolic factors. In this manner, one may further refine which genes are required for a minimal genome.

Another aspect of rational design according to further methods involves the determination of which sites within a synthetic genome may withstand insertions, such as unique identifiers (e.g., watermarks), expressible sequences of interest, etc., without disrupting gene function. In general, sites within a genome that can withstand such disruption lie at the junctions between genes, in non-coding regions, or the like.

Another aspect of rational design according to even further methods includes the selection of suitable regulatory control elements. For instance, in the case of prokaryotic-type cells, such regulatory control elements include promoters, terminators, signals for the modulation of gene expression (e.g., repressors, stimulatory factors, etc.), signals involved in translation, signals involved in modification of nucleic acids (e.g., by methylation), etc. In the case of eukaryotic-type cells, further regulatory control elements include signals involved in splicing, post-translational modification, etc.

A further design procedure that may be applied is the design of suitable cassettes to be combined to form a synthetic genome. Upon generating synthetically a substantially exact copy of a genome of known sequence, cassettes are selected which lie adjacent to one another in that sequence and, preferably, which overlap one another in order to facilitate the joining of the cassettes. Factors to be considered in designing the cassettes include, e.g., that the segments be about 4 to 6.5 kb in length, not including overlaps; that the segments contain only whole genes, except for the overlaps; and that the overlaps with adjacent sequences are about 200-250 (e.g., about 216) bp. Thus, each synthetic about 5 kb piece is a cassette comprising one or more complete genes. An illustration of cassettes that are designed, following these constraints, for the synthesis of *M. genitalium*, is shown in FIG. 1.

In another embodiment, cassettes are designed to be interchangeable, e.g., the cassettes are bounded by unique sequences such as restriction enzyme or adaptor sites, which allow the cassettes to be excised from the genome. The cassettes may be: removed, manipulated (e.g., mutated) and returned to the original location in the genome; substituted by other cassettes, such as cassettes having functionally related genes; re-assorted (rearranged) with other cassettes, for example in a combinatorial fashion; etc. Mutations or other changes may be introduced, for example, by inserting mutated nucleic acid from a natural source; by site-directed mutagenesis, either in vivo or in vitro; by synthesizing nucleic acids to contain a desired variation, etc, As noted herein, genes of interest which directly or indirectly lead to the production of desired products (e.g., therapeutic agents, biofuels, etc.) may be present in a synthetic genome. To optimize the production of such products, the genes may be manipulated and the effects of the manipulations evaluated by introducing the modified synthetic genome into a biological system. Features may be altered including, e.g., coding or regulatory sequences, codon usage, adaptations for the use of a particular growth medium, etc. Among the factors that may be evaluated are, e.g., the amount of desired end product produced, tolerance to end product, robustness, etc. Additional rounds of such manipulations and assessments may be performed to further the optimization. Using such iterative design and testing procedures (sometimes referred to herein as "reiterative" or "recursive" improvement, "recursive design," or "use of feed-back loops") one may optimize the production of a product of interest or may optimize growth of a synthetic cell. One may make predictions about cellular behavior, which may be confirmed or, if desired, modified. Furthermore, by designing and manipulating genes in a synthetic genome according to methods described herein, experimental studies may be performed, e.g., to identify features that are important for the maintenance, division, etc. of cells, features that are important to impart "life" to an organism, etc.

A variety of methods may be used to generate and assemble nucleic acid cassettes. As a first step, a cassette of interest is generally subdivided into smaller portions from which it may be assembled. Generally, the smaller portions are oligonucleotides of about between about 30 nt and about 1 kb, e.g., about 50 nt (e.g., between about 45 and about 55). In one embodiment, the oligonucleotides are designed so that they overlap adjacent oligonucleotides, to facilitate their assembly into cassettes. For example, for *M. genitalium*, the entire sequence may be divided into a list of overlapping 48-mers with 24 nucleotide overlaps between adjacent top and bottom oligonucleotides. An illustration of suitable oligonucleotides for preparing *M. genitalium* is shown in FIG. 1. The oligonucleotides may be synthesized using conventional methods and apparatus, or they may be obtained from well-known commercial suppliers.

Among the many methods which can be used to assemble oligonucleotides to form longer molecules, such as the cassettes described herein, are those described, e.g., in Stemmer et al. (1995) (Gene 164, 49-53) and Young et al. (2004) (*Nucleic Acids Research* 32, e59). One suitable method, called polymerase cycle assembly (PCA), was used by Smith et al. (2003) (*Proc Natl Acad Sci USA* 100, 15440-5) for the synthesis of the 5386 nt genome of φX174. It is generally preferable to clone and/or amplify these cassettes in order to generate enough material to manipulate readily. In some embodiments, the cassettes are cloned and amplified by conventional cell-based methods. In one embodiment, e.g., when it is difficult to clone a cassette by conventional cell-based methods, the cassettes are cloned in vitro. One such in vitro method, which is discussed in co-pending U.S. Provisional Patent Application Ser. Nos. 60/675,850; 60/722,070; and 60/725,300, uses rolling circle amplification, under conditions in which background synthesis is significantly reduced.

Cassettes which may be generated according to various exemplary methods may be of any suitable size. For example, cassettes may range from about 1 kb to about 20 kb in length. A convenient size is about 4 to about 7 kb, e.g., about 4.5 to about 6.5 kb, preferably about 5 kb. The term "about" with regard to a particular polynucleotide length, as used herein, refers to a polynucleotide that ranges from about 10% smaller than to about 10% greater than the size of the polynucleotide. In order to facilitate the assembly of cassettes, it is preferable that each cassette overlaps the cassettes on either side, e.g., by at least about 50, 80, 100, 150, 200, 250 or 1300 nt. Larger constructs (up to the size of, e.g., a minimal genome) comprising groups of such cassettes are also included, and may be used in a modular fashion according to various exemplary embodiments and methods.

A variety of methods may be used to assemble the cassettes. For example, cassettes may be assembled in vitro, using methods of recombination involving "chew-back" and repair steps, which employ either 3' or 5' exonuclease activities, in a single step or in multiple steps. Alternatively, the cassettes may be assembled with an in vitro recombination system that includes enzymes from the *Dienocuccus radiodurans* homologous recombination system. Methods of in vivo assembly may also be used.

Example II describes the generation of a synthetic mouse mitochondrial genome of 16.3 kb by the assembly of three cassettes. Example II shows the design of 682 48-mer oligonucleotides, and the assembly of those oligonucleotides into three overlapping segments (cassettes). The oligonucleotides are then assembled into cassettes, by such methods as the method described in Smith et al. (2003), supra, modified in order to reduce heat damage to the synthetic DNA.

According to one method, once a cassette is assembled, its sequence may be verified. It is usually desirable to remove errors which have arisen during the preparation of the cassettes, e.g., during the synthesis or assembly of the nucleic acid components. Among the error correction methods which may be used are; (1) methods to modify, tag and/or separate mismatched nucleotides so that amplification errors may be prevented; (2) methods of global error correction, using enzymes to recognize and cleave mismatches in DNA, having known or unknown sequences, to produce fragments from which the errors may be removed and the remaining error-free pieces reassembled; (3) methods of site-directed mutagenesis; and (4) methods to identify errors, select portions from independent synthetic copies which are error-free, and assemble the error-free portions, e.g., by overlap extension PCR (OE-PCR). Other methods to recognize errors include, e.g., the use of isolated mismatch or mutation recognition proteins, hybridization of oligonucleotide-fluorescent probe conjugates, electrophoretic/DNA chip methods, and differential chemical cleavage with reagents assaying for base access ability either in solution or the solid phase; such methods may be combined with conventional procedures to remove errors.

In one embodiment, one or more identifying features, such as a unique sequence (e.g., encoding a particular symbol or name, or, e.g., spelling with the alphabet letter designations for the amino acids) or an identifiable mutation which does not disrupt function are introduced into the synthetic genome. Such sequences, sometimes referred to herein as "watermarks," may serve not only to show that the genome has, in fact, been artificially synthesized and to enable branding and tracing, but also to distinguish the synthetic genome from naturally occurring genomes. Often, genes or cassettes contain selectable markers, such as drug resistance markers, which aid in selecting nucleic acids that comprises the genes or cassettes. The presence of such selectable markers may also distinguish the synthetic genomes from naturally occurring nucleic acids. A synthetic genome which is identical to a naturally occurring genome, but which contains one or more identifying markers as above, is sometimes referred to herein as being "substantially identical" to the naturally occurring genome.

A synthetic genome according to one embodiment may be present in any environment that allows for it to function. For example, a synthetic genome may be present in (e.g., introduced into) any of the biological systems described herein, or others. The functions and activities of a synthetic genome, and the consequences of modifying elements of the genome, can be studied in a suitable biological system. Furthermore, a suitable biological system allows proteins of interest (e.g., therapeutic agents) to be produced. In some embodiments, if suitable substrates are provided, downstream, non-proteinaceous products, such as energy sources (e.g., hydrogen or ethanol) may also be produced, e.g., in commercially useful amounts.

A variety of suitable biological systems may be used according to various embodiments and methods. For example, in one embodiment, a synthetic genome is contacted with a solution comprising a conventional coupled transcription/translation system. In such a system, the nucleic acid may be able to replicate itself, or it may be necessary to replenish the nucleic acid, e.g., periodically.

In another embodiment, a synthetic genome is introduced into a vesicle such that the genome is encapsulated by a protective lipid-based material. In one embodiment, the synthetic genome is introduced into a vesicle by contacting the synthetic genome, optionally in the presence of desirable cytoplasmic elements such complex organelles (e.g., ribosomes) and/or small molecules, with a lipid composition or with a combination of lipids and other components of functional cell membranes, under conditions in which the lipid components encapsulate the synthetic genome and other optional components to form a synthetic cell. In other embodiments, a synthetic genome is contacted with a coupled transcription/translation system and is then packaged into a lipid-based vesicle. In a further embodiment, the internal components are encapsulated spontaneously by the lipid materials.

Exemplary embodiments also include a synthetic genome introduced into a recipient cell, such as a bacterial cell, from which some or all of the resident (original) genome has been removed. For example, the entire resident genome may be removed to form a ghost cell (a cell devoid of its functional natural genome) and the resident genome may be replaced by the synthetic genome. Alternatively, a synthetic genome may be introduced into a recipient cell which contains some or all of its resident genome. Following replication of the cell, the resident (original) and the synthetic genome will segregate, and a progeny cell will form that contains cytoplasmic and other epigenetic elements from the cell, but that contains, as the sole genomic material, the synthetic genome (e.g., a copy of a synthetic genome). Such a cell is a synthetic cell according to various embodiments and methods, and differs from the recipient cell in certain characteristics, e.g., nucleotide sequence, nucleotide source, or non-nucleotide biochemical components.

A variety of in vitro methods may be used to introduce a genome (synthetic, natural, or a combination thereof) into a cell. These methods include, e.g., electroporation, lipofection, the use of gene guns, etc. In one embodiment, a genome, such as a synthetic genome, is immobilized in agar; and the agar plug is laid on a liposome, which is then inserted into a host cell. In some embodiments, a genome is treated to fold and compress before it is introduced into a cell. Methods for inserting or introducing large nucleic acid molecules, such as bacterial genomes, into a cell are sometimes referred to herein as chromosome transfer, transport, or transplantation.

According to one embodiment; a synthetic cell may comprise elements from a host cell into which it has been introduced, e.g., a portion of the host genome, cytoplasm, ribosomes, membrane, etc. In another embodiment, the components of a synthetic cell are derived entirely from products encoded by the genes of the synthetic genome and by products generated by those genes. Of course, nutritive, metabolic and other substances as well as physical conditions such as light and heat may be provided externally to facilitate the growth, replication and expression of a synthetic cell.

Various exemplary methods may be readily adapted to computer-mediated and/or automated (e.g., robotic) formats. Many synthetic genomes (including a variety of combinatorial variants of a synthetic genome of interest) may be prepared and/or analyzed simultaneously, using high throughput methods. Automated systems for performing various methods as described herein are included. An automated system permits design of a desired genome from genetic components by selection using a bioinformatics computer system, assembly and construction of numerous genomes and synthetic cells, and automatic analysis of their characteristics, feeding back to suggested design modifications.

While various embodiments and methods have been described herein, it should be understood that they have been presented by way of example only, and not limitation. Further, the breadth and scope of a preferred embodiment should not be limited by any of the above-described exemplary embodiments.

In the foregoing and in the following example, all temperatures are set forth in uncorrected degrees Celsius; and, unless otherwise indicated, all parts and percentages are by weight.

EXAMPLES

Example I—*Mycoplasma* Comparative Genomics to Identify Genes in a Minimal Gene Set

*Mycoplasma* Comparative Genomics.

The 13 complete and 2 partial genome sequences currently in the inventors' dataset comprise an in silico laboratory.

Comparisons of pairs of *mycoplasma* genomes using the whole genome alignment tool MUMMER shows between species that are closely related such as *M. capricolum, M. mycoides* SC, and *Mycoplasma florum*, genome rearrangements are symmetrical about an axis passing through the origins of replication and points that bisect the genome equally. The direction of transcription of rearranged genes almost always stays the same relative to the origin of replication. This phenomenon has been observed for other species bacteria but perhaps never so strikingly as with *M. capricolum* and *M. mycoides* SC (see FIG. 2). These reciprocal crossovers suggest that any major removal of DNA from one side of the genome might need to be matched with a similar deletion from the other side so that the terminus of replication remains constant.

Core *Mycoplasma* Gene Set.

The 13 complete genome sequences include 5 species from the *pneumoniae* branch of *Mollicutes* phylogeny, 4 from the *hominis* branch, three from the *Entomoplasmatales* branch and one from the *Acholeplasmatales* branch. For each of the complete genomes we used BLASTp to generate orthologs tables based on whether gene X in one genome has a significant best BLASTp hit to gene Y in another genome, and Y is X's best hit, then those genes are called orthologs. Using these tables, we identified a core *mycoplasma* gene set, i.e. those orthologous genes common to all 13 completely sequenced *mycoplasma* species. Additionally, those tables identify orthologous gene sets for three of the main *mycoplasma* tree branches.

The core *mycoplasma* gene set is 165 genes. That set can be expanded to ~200 by including those 45 genes missing only in the intracellular parasite *Phytoplasma asteris*, which obtains many of its essential metabolic products from the plant cytoplasm this species lives in. The set can be further expanded to ~310 genes by taking into account non-orthologous gene displacements that are obvious in some cases and suggested in others. Obvious examples include the 14 genes absent in either or both of the two non-glycolytic species *Ureaplasma parvum* or *Mycoplasma arthritides*. An additional 96 genes are included in the expanded core gene set because orthologs-are absent in only one of the 12 complete genome (*P. asteris* is so different from the other species it is usually ignored in this core set expansion process). Based on this 13 genome comparative genomics analysis only, we would predict that our model synthetic organism, *M. laboratorium*, would need only about 310 genes and would have a genome containing only about 372 kbp.

Given the significant evolutionary divergences of the 4 branches of mycoplasmas from each other because of their high rate of evolution and different responses to gene loss, we also determined the common gene sets for the *pneumoniae, hominis* and *Entomoplasmatales* groups of mycoplasmas. (See Table 1, below). It is instructive to consider an expanded core gene set for the 5 members of the *pneumoniae* group (which includes *M genitalium*, our planned platform for *M. laboratorium* construction). If one includes only those genes present in at least 4 of the 5 group member genomes; that expanded core set is 391 protein coding genes.

TABLE 1

Sizes of the orthologous gene sets shared by all and various subgroups of the mycoplasmas

| Orthologous gene sets | *M. genitalium* | *M. arthritldis* | *M .capricolum* |
|---|---|---|---|
| Gene in all mycoplasmas | 165 | 168 | 152 |
| Genes in all mycoplasmas and *B. subtilis* and *C. perfringens* | 153 | 159 | 151 |
| Genes in all mycoplasmas except Onion Yellows Phytoplasma | 200 | 206 | 197 |
| Core mycoplasma genes lost in Onion Yellows Phytoplasma | 35 | 38 | 39 |
| Genes present in all 5 pneumoniae Glade members | 294 | — | — |
| Genes present in all 5 pneumoniae Glade members and in hominis group | 220 | 220 | — |
| Genes present in all 5 pneumoniae clade members and in mycoides group | 244 | — | 236 |
| Genes present in all 5 pneumoniae clade members and in *P. asteris* | 207 | — | — |
| Genes present in all 4 hominis clade members | 293 | — | — |
| Genes present in all hominis clade members and in mycoides group | 243 | — | — |
| Genes present in all hominis clade members and in *Phytoplasma asteris* | — | 206 | — |
| Genes present in all 3 mesoplasma/mycoides clade members | — | — | 438 |
| Genes present in all mycoides clade members and in *Phytoplasma asteris* | — | — | 230 |
| *M. capricolum* orthologs in *M. mycoides* | — | — | 715 |

Example II—Synthesis of a Mouse Mitochondrial Genome

The mouse mitochondrial genome is a 16,299 bp circular DNA and its sequence has been critically checked. We designed 682 48-mers to assemble it in three overlapping segments; S1 (6,528 bp), S2 (5,328 bp), and S3 (4,508 bp) as diagrammed in FIG. 3A.

We assembled each of these three pieces by the method described in Smith et al. (2003), supra, modified to reduce the heating damage to the synthetic product. The gel shown in FIG. 3B illustrates products from one such modified procedure that dramatically reduces the time spent at high temperature.

The synthesis of three overlapping segments comprising the entire mouse mitochondrial genome illustrates that combinations of PCA and PCR can routinely assemble 5-6 Kris Prather segments of DNA and validates our plan to build 5 Kris Prather cassettes for the assembly of a cellular genome.

Example III—Synthesis of 5 kb Cassettes of an Essential Region of the *M. genitalium* Genome 5 kb cassettes are constructed to generate a synthetic copy of an essential region of the *M. genitalium* genome—the ribosomal protein genes MG149.1 through MG181. This 18.5 kb region is flanked by genes that tolerate transposon insertions (MG149 and MG182). Sets of 386 top strand and 386 bottom strand oligonucleotides, of 48 nt, were synthesized to cover this region. These nucleic acids are illustrated in FIG. 4.

The assembly of four overlapping segments (cassettes) comprising these oligonucleotides is performed.

Using these techniques, cassettes of, for example, 4-6 kb can be constructed that include gene sets of interest (e.g. a minimal genome from a unicellular microorganism), and can be "mixed and matched" with, or altered by substitutions from, e.g., other species, to obtain a custom made genome, which can be introduced into a vesicle or ghost cell for testing, as described above. Synthetic cells thus constructed can be cultured under suitable conditions to determine function. After determination of functionality, the genome can be modified by substitution of cassettes, and the process repeated until a desired result is obtained.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding specific embodiments are to be construed as merely illustrative, and not as limiting the scope of the invention in any way whatsoever. The entire disclosure of all applications, patents and publications cited above and in the figures are hereby incorporated by reference.

What is claimed is:

1. A method for assembling a nucleic acid construct comprising:
   (a) generating a plurality of double-stranded nucleic acid cassettes from chemically synthesized oligonucleotides or copies thereof,
      wherein the cassettes comprise adjacent regions of a nucleic acid construct to be assembled and wherein each of the cassettes overlap with one or more other cassette(s) by at least 50 nucleotides and is between about 4 kb and 7 kb in length, not including the overlaps; and
   (b) simultaneously assembling the plurality of nucleic acid cassettes in vitro in a chew back and repair step utilizing:
      an enzyme having 3' or 5' exonuclease activity,
      a DNA polymerase,
      polyethylene glycol (PEG) or a single-stranded binding protein, and
      a ligase
   thereby assembling the nucleic acid construct.

2. The method of claim 1 wherein the enzyme having exonuclease activity is a 5' exonuclease and the step (b) utilizes PEG.

3. The method of claim 2 wherein the assembly is performed in a single step.

4. The method of claim 2 wherein the plurality of nucleic acid cassettes comprises more than 4 nucleic acid cassettes.

5. The method of claim 4 wherein the plurality of nucleic acid cassettes comprises more than 6 nucleic acid cassettes.

6. The method of claim 2, wherein the cassettes are from about 4.5 kilobases to about 6.5 kilobases in length, not including overlaps.

7. The method of claim 2, wherein the cassettes are about 5 kilo bases in length, not including overlaps.

8. The method of claim 2, wherein each of the cassettes overlaps an adjacent cassette by at least 200 nucleotides.

9. The method of claim 1, wherein the assembled nucleic acid construct is a non-naturally occurring genome nucleic acid construct.

10. The method of claim 1, wherein one or more of the cassettes includes restriction enzyme sites or adaptor sites.

11. The method of claim 1, wherein each cassette is generated entirely from chemically synthesized oligonucleotides or copies thereof.

12. The method of claim 2, wherein the method is automated.

13. The method of claim 1, wherein generating the cassettes comprises ligating the chemically synthesized oligonucleotides to form ligation products and performing cycles of polymerase cycle assembly (PCA) on the ligation products, thereby forming PCA products.

14. The method of claim 13, wherein the PCA consists of 5 cycles of PCA and the ligation is performed at 50° C.

15. The method of claim 1, wherein step (a) further comprises cloning or amplifying the cassettes.

16. The method of claim 1, wherein the chemically synthesized oligonucleotides or copies thereof are between about 30 nucleotides and 1 kilo base in length.

17. The method of claim 1, wherein each of the cassettes overlaps an adjacent cassette by about 50-1300 nucleotides.

18. The method of claim 1 wherein the plurality of nucleic acid cassettes comprises at least 4 nucleic acid cassettes.

19. The method of claim 18 wherein the plurality of nucleic acid cassettes comprises more than 6 nucleic acid cassettes.

20. The method of claim 1, wherein the cassettes are from about 4.5 kilobases to about 6.5 kilobases in length, not including overlaps.

21. The method of claim 1, wherein each of the cassettes overlaps an adjacent cassette by at least 200 nucleotides.

* * * * *